(12) United States Patent
Nieto et al.

(10) Patent No.: US 10,350,055 B2
(45) Date of Patent: *Jul. 16, 2019

(54) TEXTURED BREAST IMPLANT AND METHODS OF MAKING SAME

(71) Applicant: Allergan, Inc., Irvine, CA (US)

(72) Inventors: Robert Nieto, Santa Barbara, CA (US); Zachary Dominguez, Santa Barbara, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/147,472

(22) Filed: Sep. 28, 2018

(65) Prior Publication Data

US 2019/0029807 A1 Jan. 31, 2019

Related U.S. Application Data

(63) Continuation of application No. 14/703,307, filed on May 4, 2015, now Pat. No. 10,092,392.

(60) Provisional application No. 61/994,767, filed on May 16, 2014.

(51) Int. Cl.
*A61F 2/12* (2006.01)
*A61F 2/30* (2006.01)
*A61F 2/00* (2006.01)

(52) U.S. Cl.
CPC ........ *A61F 2/12* (2013.01); *A61F 2002/0081* (2013.01); *A61F 2210/0076* (2013.01); *A61F 2240/001* (2013.01); *A61F 2250/0026* (2013.01); *A61F 2250/0051* (2013.01)

(58) Field of Classification Search
CPC ... A61F 2/12; A61F 2/0077; A61F 2002/3084
USPC .................... 623/8; 427/2.24, 180
See application file for complete search history.

(56) References Cited

U.S. PATENT DOCUMENTS

| | | |
|---|---|---|
| 2,762,476 A | 9/1956 | Barnett |
| 2,805,208 A | 9/1957 | Roche |
| 3,189,921 A | 6/1965 | Pangman |
| 3,293,663 A | 12/1966 | Cronin |
| 3,366,975 A | 2/1968 | Panaman |
| 3,559,214 A | 2/1971 | Pangman |
| 3,600,718 A | 8/1971 | Boone |
| 3,665,520 A | 5/1972 | Perras et al. |
| 3,700,380 A | 10/1972 | Kitrilakis |

(Continued)

FOREIGN PATENT DOCUMENTS

| | | |
|---|---|---|
| CA | 2049377 | 3/1992 |
| CN | 2587376 | 11/2003 |

(Continued)

OTHER PUBLICATIONS

Nace. A Surface Texture Modeling System for Solid Freeform Fabrication. Massachusetts Institute of Technology Sep. 1997 Year: (1997).*

(Continued)

*Primary Examiner* — Cachet I Sellman
(74) *Attorney, Agent, or Firm* — Nathan S. Smith; Morgan, Lewis & Bockius LLP

(57) ABSTRACT

Methods for texturing surgical implants, for example, breast implants, are provided. The methods include the use of computer controlled 3D printing of a sacrificial material to create a textured surface on an unfinished surface of the implant.

20 Claims, 2 Drawing Sheets

(56) References Cited

U.S. PATENT DOCUMENTS

| | | |
|---|---|---|
| 3,852,832 A | 12/1974 | McGhan et al. |
| 3,934,274 A | 1/1976 | Hartley, Jr. |
| 4,034,751 A | 7/1977 | Hung |
| 4,157,085 A | 6/1979 | Austad |
| 4,231,979 A | 11/1980 | White et al. |
| 4,237,237 A | 12/1980 | Jarre et al. |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks et al. |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein et al. |
| 4,499,211 A | 2/1985 | Walch et al. |
| 4,531,244 A | 7/1985 | Hamas |
| 4,573,999 A | 3/1986 | Netto |
| 4,584,324 A | 4/1986 | Bauman et al. |
| 4,592,755 A | 6/1986 | Penton et al. |
| 4,608,396 A | 8/1986 | Bauman et al. |
| 4,610,690 A | 9/1986 | Tiffany |
| 4,636,213 A | 1/1987 | Pakiam |
| 4,643,733 A | 2/1987 | Becker |
| 4,647,618 A | 3/1987 | Bauman et al. |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl et al. |
| 4,740,208 A | 4/1988 | Cavon |
| 4,772,285 A | 9/1988 | Ksander et al. |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl et al. |
| 4,803,025 A | 2/1989 | Brockmeyer |
| 4,828,560 A | 5/1989 | Heyler, III |
| 4,840,628 A | 6/1989 | Cavon |
| 4,841,992 A | 6/1989 | Sasaki et al. |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A * | 9/1990 | Ersek .................. A61F 2/12 623/23.74 |
| 4,960,425 A | 10/1990 | Yan et al. |
| 4,965,430 A | 10/1990 | Curtis et al. |
| 4,969,899 A | 11/1990 | Cox, Jr. |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan et al. |
| 5,026,394 A | 6/1991 | Baker |
| 5,034,422 A | 7/1991 | Triolo et al. |
| 5,035,249 A | 7/1991 | Sasaki et al. |
| 5,092,348 A | 3/1992 | Dubrul et al. |
| 5,092,882 A | 3/1992 | Lynn et al. |
| 5,104,409 A | 4/1992 | Baker |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn et al. |
| 5,158,571 A | 10/1992 | Picha |
| 5,158,573 A | 10/1992 | Berg |
| 5,171,269 A | 12/1992 | Bark |
| 5,185,297 A | 2/1993 | Park et al. |
| 5,204,024 A | 4/1993 | Onaka et al. |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,340,656 A | 8/1994 | Sachs et al. |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk et al. |
| 5,383,929 A | 1/1995 | Ledergerber |
| 5,437,824 A | 8/1995 | Carlisle et al. |
| 5,441,919 A | 8/1995 | Park et al. |
| 5,447,535 A | 9/1995 | Muller |
| 5,455,100 A | 10/1995 | White |
| 5,480,430 A | 1/1996 | Carlisle et al. |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A * | 6/1996 | Iversen .................. A61F 2/0077 264/131 |
| 5,534,023 A | 7/1996 | Henley |
| 5,545,217 A | 8/1996 | Offray et al. |
| 5,545,220 A | 8/1996 | Andrews et al. |
| 5,549,671 A | 8/1996 | Waybright et al. |
| 5,571,179 A | 11/1996 | Manders et al. |
| RE35,391 E | 12/1996 | Brauman |
| 5,589,176 A | 12/1996 | Seare, Jr. |
| 5,605,693 A | 2/1997 | Seare, Jr. |
| 5,607,473 A | 3/1997 | Weber-Unger et al. |
| 5,624,674 A | 4/1997 | Seare, Jr. |
| 5,630,843 A | 5/1997 | Rosenberg |
| 5,630,844 A | 5/1997 | Dogan et al. |
| 5,653,755 A | 8/1997 | Ledergerber |
| 5,658,330 A | 8/1997 | Carlisle et al. |
| 5,674,285 A | 10/1997 | Quaid |
| 5,681,572 A | 10/1997 | Seare, Jr. |
| 5,776,159 A | 7/1998 | Young |
| 5,779,734 A | 7/1998 | Ledergerber |
| 5,798,065 A | 8/1998 | Picha |
| 5,824,081 A | 10/1998 | Knapp et al. |
| 5,843,189 A | 12/1998 | Perouse |
| 5,855,588 A | 1/1999 | Young |
| 5,871,497 A | 2/1999 | Young |
| 5,895,423 A | 4/1999 | Becker et al. |
| 5,935,164 A | 8/1999 | Iversen |
| 5,961,552 A | 10/1999 | Iversen et al. |
| 5,964,803 A | 10/1999 | Iversen et al. |
| 5,965,076 A | 10/1999 | Banks et al. |
| 5,984,943 A | 11/1999 | Young |
| 5,993,716 A | 11/1999 | Draenert |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura, Jr. |
| 6,113,634 A | 9/2000 | Weber-Unger et al. |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg et al. |
| 6,214,045 B1 | 4/2001 | Corbitt, Jr. et al. |
| 6,214,926 B1 | 4/2001 | Winn et al. |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray et al. |
| 6,464,726 B1 | 10/2002 | Heljenek |
| 6,520,989 B1 | 2/2003 | Eaton |
| 6,531,523 B1 | 3/2003 | Davankov et al. |
| 6,544,287 B1 | 4/2003 | Johnson et al. |
| 6,602,452 B2 | 8/2003 | Schuessler |
| 6,605,116 B2 | 8/2003 | Falcon et al. |
| 6,638,308 B2 | 10/2003 | Corbitt, Jr. et al. |
| 6,673,285 B2 | 1/2004 | Ma |

(56) References Cited

U.S. PATENT DOCUMENTS

| | | |
|---|---|---|
| 6,692,527 B1 | 2/2004 | Bellin et al. |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. et al. |
| 6,900,055 B1 | 5/2005 | Fuller et al. |
| 6,913,626 B2 | 7/2005 | McGhan |
| 6,916,339 B1 | 7/2005 | Missana et al. |
| 6,921,418 B2 | 7/2005 | Ledergerber |
| 6,932,840 B1 | 8/2005 | Bretz |
| 6,993,406 B1 * | 1/2006 | Cesarano, III ............ A61F 2/28 424/422 |
| 7,081,135 B2 | 7/2006 | Smith et al. |
| 7,081,136 B1 | 7/2006 | Becker |
| 7,105,116 B2 | 9/2006 | Bellin et al. |
| 7,169,180 B2 | 1/2007 | Brennan |
| 7,192,450 B2 | 3/2007 | Brauker et al. |
| 7,244,270 B2 | 7/2007 | Lesh |
| 7,309,232 B2 | 12/2007 | Rutherford et al. |
| 7,323,208 B2 | 1/2008 | Ma et al. |
| 7,476,249 B2 | 1/2009 | Frank |
| 7,520,896 B2 | 4/2009 | Benslimane |
| 7,547,393 B2 | 6/2009 | Ramaswamy et al. |
| 7,625,405 B2 | 12/2009 | Purkait |
| 7,632,228 B2 | 12/2009 | Brauker et al. |
| 7,632,291 B2 | 12/2009 | Stephens et al. |
| 7,641,688 B2 | 1/2010 | Lesh |
| 7,645,475 B2 * | 1/2010 | Prewett ................ A61F 2/0077 427/180 |
| 7,758,788 B2 | 7/2010 | Job |
| 7,867,061 B2 | 1/2011 | Elshout |
| 8,202,317 B2 | 6/2012 | Becker |
| 8,313,527 B2 | 11/2012 | Powell et al. |
| 8,506,627 B2 | 8/2013 | Van Epps et al. |
| 8,546,458 B2 | 10/2013 | Thompson et al. |
| 8,728,159 B2 | 5/2014 | Kim |
| 8,765,039 B1 | 7/2014 | Ledergerber |
| 2002/0038147 A1 | 3/2002 | Miller |
| 2002/0193885 A1 | 12/2002 | Leaeay et al. |
| 2003/0036803 A1 | 2/2003 | McGhan |
| 2003/0093151 A1 | 5/2003 | Zhang |
| 2003/0105469 A1 | 6/2003 | Karmon |
| 2003/0129717 A1 | 7/2003 | Becker et al. |
| 2003/0205846 A1 | 11/2003 | Bellin et al. |
| 2003/0208269 A1 | 11/2003 | Eaton et al. |
| 2004/0010225 A1 | 1/2004 | Schuessler |
| 2004/0115241 A1 | 6/2004 | Calhoun et al. |
| 2004/0127985 A1 | 7/2004 | Bellin et al. |
| 2004/0137032 A1 | 7/2004 | Wang |
| 2004/0143327 A1 | 7/2004 | Ku |
| 2004/0148024 A1 | 7/2004 | Williams |
| 2004/0153151 A1 | 8/2004 | Gonzales de Vicente |
| 2004/0176493 A1 | 9/2004 | Ferguson |
| 2004/0213986 A1 | 10/2004 | Kim et al. |
| 2005/0055093 A1 | 3/2005 | Brennan |
| 2005/0070124 A1 | 3/2005 | Miller et al. |
| 2005/0112169 A1 | 5/2005 | Brauker et al. |
| 2005/0122169 A1 | 6/2005 | Watanabe |
| 2005/0175702 A1 | 8/2005 | Muller-Schulte |
| 2005/0196452 A1 | 9/2005 | Boyan et al. |
| 2005/0216094 A1 | 9/2005 | Prewett |
| 2005/0251083 A1 | 11/2005 | Carr-Brendel et al. |
| 2006/0002810 A1 | 1/2006 | Grohowski |
| 2006/0036266 A1 | 2/2006 | Sulamanidze et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma et al. |
| 2006/0257377 A1 | 11/2006 | Atala et al. |
| 2007/0093911 A1 | 4/2007 | Fricke et al. |
| 2007/0104693 A1 | 5/2007 | Quijano et al. |
| 2007/0104695 A1 | 5/2007 | Quijano et al. |
| 2007/0116735 A1 | 5/2007 | Calhoun et al. |
| 2007/0135916 A1 | 6/2007 | Maxwell et al. |
| 2007/0154525 A1 | 7/2007 | Calhoun et al. |
| 2007/0190108 A1 | 8/2007 | Datta et al. |
| 2007/0198085 A1 | 8/2007 | Benslimane |
| 2008/0009830 A1 | 1/2008 | Fujimoto et al. |
| 2008/0071371 A1 | 3/2008 | Elshout |
| 2008/0075752 A1 | 3/2008 | Ratner et al. |
| 2008/0095823 A1 | 4/2008 | Williams et al. |
| 2008/0154366 A1 | 6/2008 | Frank |
| 2008/0241212 A1 | 10/2008 | Moses et al. |
| 2008/0268019 A1 | 10/2008 | Badylak et al. |
| 2008/0312739 A1 | 12/2008 | Agerup et al. |
| 2009/0045166 A1 | 2/2009 | Li |
| 2009/0082864 A1 | 3/2009 | Chen et al. |
| 2009/0087641 A1 | 4/2009 | Favis et al. |
| 2009/0093878 A1 | 4/2009 | Glicksman |
| 2009/0118829 A1 * | 5/2009 | Powell ...................... A61F 2/12 623/8 |
| 2009/0125107 A1 | 5/2009 | Maxwell |
| 2009/0148829 A1 | 6/2009 | Ecker et al. |
| 2009/0169716 A1 | 7/2009 | Linhardt et al. |
| 2009/0198331 A1 | 8/2009 | Kesten et al. |
| 2009/0198332 A1 | 8/2009 | Becker |
| 2009/0198333 A1 | 8/2009 | Becker |
| 2010/0042211 A1 | 2/2010 | Van Epps et al. |
| 2010/0075056 A1 | 3/2010 | Axisa et al. |
| 2010/0292790 A1 * | 11/2010 | Stroumpoulis ....... A61F 2/0077 623/8 |
| 2011/0054605 A1 | 3/2011 | Becker |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0172798 A1 * | 7/2011 | Staiger .................... A61L 27/04 700/98 |
| 2011/0196488 A1 | 8/2011 | Goraltchouk et al. |
| 2011/0196489 A1 | 8/2011 | Van Epps et al. |
| 2011/0257623 A1 | 10/2011 | Marshall et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0309541 A1 * | 12/2011 | Thompson .............. A61L 27/18 264/46.6 |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077891 A1 | 3/2012 | Liu et al. |
| 2012/0101574 A1 | 4/2012 | Goraltchouk et al. |
| 2012/0245685 A1 | 9/2012 | Yu |
| 2012/0321777 A1 | 12/2012 | Stroumpoulis et al. |
| 2013/0013062 A1 | 1/2013 | Thompson et al. |
| 2013/0023987 A1 | 1/2013 | Liu et al. |
| 2013/0032962 A1 | 2/2013 | Liu et al. |
| 2013/0034633 A1 | 2/2013 | von Hassein |
| 2013/0053956 A1 | 2/2013 | Powell et al. |
| 2013/0158657 A1 | 6/2013 | Nofrey et al. |
| 2013/0209661 A1 | 8/2013 | Goraltchouk et al. |
| 2013/0245148 A1 | 9/2013 | Thompson et al. |
| 2013/0261745 A1 | 10/2013 | Van Epps |
| 2013/0302511 A1 | 11/2013 | Goraltchouk et al. |
| 2013/0310934 A1 | 11/2013 | Van Epps et al. |
| 2016/0022866 A1 | 1/2016 | Liu et al. |
| 2016/0151542 A1 | 6/2016 | Liu et al. |
| 2018/0092726 A1 | 4/2018 | Van Epps et al. |

FOREIGN PATENT DOCUMENTS

| | | |
|---|---|---|
| EP | 230672 | 8/1987 |
| EP | 293256 | 11/1988 |
| EP | 315814 | 5/1989 |
| EP | 332371 | 9/1989 |
| EP | 710468 | 5/1996 |
| EP | 522585 | 10/1996 |
| EP | 1532942 | 5/2005 |
| EP | 1847369 | 10/2007 |

(56) References Cited

FOREIGN PATENT DOCUMENTS

| | | | |
|---|---|---|---|
| FR | 2840617 | 12/2003 | |
| GB | 1022736 | 3/1966 | |
| GB | 2225016 | 5/1990 | |
| JP | 2003-062062 | 3/2003 | |
| JP | 2007-029717 | 2/2007 | |
| MX | 2012012801 | 5/2014 | |
| RU | 2340308 | 12/2008 | |
| WO | WO-9014927 A1 * | 12/1990 | ............ B24C 1/003 |
| WO | WO 97/15242 | 5/1997 | |
| WO | WO 98/10803 | 3/1998 | |
| WO | WO 98/42318 | 10/1998 | |
| WO | WO 00/24437 | 5/2000 | |
| WO | WO 00/56376 | 9/2000 | |
| WO | WO 2004/037318 | 5/2004 | |
| WO | WO 2004/062531 | 7/2004 | |
| WO | WO 2005/020849 | 3/2005 | |
| WO | WO 2006/133366 | 12/2006 | |
| WO | WO 2008/001591 | 1/2008 | |
| WO | WO 2009/061672 | 5/2009 | |
| WO | WO 2009/110917 | 9/2009 | |
| WO | WO 2010/019292 | 2/2010 | |
| WO | WO 2010/019761 | 2/2010 | |
| WO | WO 2010/136840 | 12/2010 | |
| WO | WO 2011/066441 | 6/2011 | |
| WO | WO 2011/094155 | 8/2011 | |
| WO | WO 2011/097499 | 8/2011 | |
| WO | WO 2013/184569 | 12/2013 | |

OTHER PUBLICATIONS

Alvarez, et al, "Synthesis of Macro/Mesoporous Silica and Carbon Monoliths by Using a Commercial Polyurethane Foam as Sacrificial Template," Material Letters, 2007, 2378-2381, 61.

Barnsley, et al, "Textured Surface Breast Implants in the Prevention of Capsular Contracture Among Breast Augmentation Patients: A Meta-Analysis of Randomized Controlled Trials, Plastic and Reconstructive Surgery," 2006, 2182-2190, 117(7).

Barr, "Current Implant Surface Technology: An Examination of Their Nanostructure and Their Influence on Fibroblast Alignment and Biocompatibility," J. of Plastic Surgery, 2009, 198-217, 9.

Brauker, et al, "Neovascularization of Synthetic Membranes Directed by Membrane Microarchitecture," Journal of Biomedical Materials Research, 1995, 1517-1524, 29, John Wiley & Sons, Inc.

Brohim, et al, "Early Tissue Reaction to Textured Breast Implant Surfaces," Ann Plast Surg, 1992, 354-362, 28.

Capes et al., "Fabrication of polymeric scaffolds with a controlled distribution of pores," J of Materials Science: Materials in Medicine, Dec. 2005, vol. 16, No. 12, DD 1069-1075.

Inamed Aesthetics Brochure, Directions for Use Style 410 Silicone-Filled Breast Implants (2003), 23 pages.

Kim et al., "Modified release of coated sugar spheres using drug-containing polymeric dispersions," Archives Pharmacal Research, 2007, vol. 30, No. 1, pp. 124-130.

Ma, "Scaffolds for Tissue Fabrication," Materials Today, 2004, 30-40, 7.

Mikos, "Formation of Highly Porous Biodegradable Scaffolds for Tissue Engineering," Journal of Biotechnology, Aug. 15, 2000, 114-119, 3(2).

Minami, "The Composition and Behavior of Capsules Around Smooth and Textured Breast Implants in Pigs," Plast. Reconstr. Surg., 2006, 874-884, 118.

Murphy, et al, "Salt Fusion: An Approach to Improve Pore Interconnectivity Within Tissue Engineering Scaffolds," Tissue Engineering, 2002, 43-52, 8 (1).

Sharkawy, "Engineering the Tissue Which Encapsulates Subcutaneous Implants. II. Plasma-tissue Exchange Properties," John Wiley & Sons, 1998, DD 586-597.

Wei, et al, Macroporous and Nanofibrous Polymer Scaffolds and Polymer/Bone-Like Apatite Composite Scaffolds Generated by Sugar Spheres, Journal of Biomedical Materials Research, 2006, 306-315, 78A.

Yu et al., "Softness measurement for open-cell foam materials and human soft tissue," Measurement Science and Technology, 2006, vol. 17, pp. 1785-1791.

Zhang, "Macroporous Alumina Monoliths Prepared by Filling Polymer Foams with Alumina Hydrosols," Journal of Materials Science, 2009, vol. 44, No. 3, pp. 931-938.

* cited by examiner

TEXTURED BREAST IMPLANT AND METHODS OF MAKING SAME

CROSS-REFERENCE TO RELATED APPLICATIONS

This application a continuation of U.S. patent application Ser. No. 14/703,307, filed on May 4, 2015, which claims the benefit of U.S. Provisional Patent Application No. 61/994,767, filed on May 16, 2014, the entirety of each of which is incorporated by reference herein

BACKGROUND

The present invention is generally directed to implantable devices, and is more specifically directed to breast implants and methods for creating a textured surface on breast implants.

Breast implants are well known for use in breast reconstruction and for aesthetic purposes, for example, to improving the appearance of the breast. Such implants typically comprise a flexible silicone shell which makes up outer surface of the implant. The shell surrounds a silicone gel or saline filling. Many commercially available implants include so-called "textured surfaces" on the outer surface of the shell. Such textured surfaces are purposefully made to interact with the breast tissue in a healthy manner. Among other things, the type of texture may influence tissue ingrowth and reduce the occurrence of capsular contracture, an adverse event sometimes associated with breast implants.

Several methods for creating a textured surface on an implant currently exist. One method is to use a sacrificial material, for example, salt particles. Salt particles are applied to a silicone shell as the shell is being molded on a mandrel. The particles take up space within the silicone material as the material is being cured. When the sacrificial material is removed (dissolved, melted, etc.), the shell surface has a negative imprint of the original structure of the particles.

Despite many advances in the construction of breast implants, there remains a need for better texturing methods. There has been an interest in developing an optimally textured surface that will affect the breast tissue in the healthiest manner.

SUMMARY

The present invention provides improved methods of making textured surfaces for breast implants. In one embodiment, a method for creating a textured surface on a breast implant generally comprises providing a breast implant shell, applying a tacky silicone layer on the shell, using a computer-controlled deposit mechanism to deposit a texturing material in a predetermined manner onto the tacky silicone layer and removing the texturing material from the tacky silicone layer to obtain a textured surface.

The step of using a computer-controlled deposit mechanism may comprise depositing onto the tacky silicone layer a predetermined number of successive layers of the texturing material. Further, a binder may be applied to one or more predetermined regions of each successive layer of texturing material to cause the texturing material to become bonded at said one or more predetermined regions.

In one embodiment, the texturing material is a sugar. The binder may be an aqueous solution or alcohol.

In another embodiment, the method further comprises the step of applying an additional silicone layer to the deposited layers of texturing material.

BRIEF DESCRIPTION OF THE DRAWINGS

The present invention may be more readily understood, and the numerous aspects and advantages thereof better appreciated, with reference to the following Detailed Description and accompanying Drawings of which.

DETAILED DESCRIPTION

Generally, the present invention provides a breast implant, or other soft implant, comprising a shell, for example, a silicone elastomer shell, with a textured surface, and methods for making such implants and textured surfaces. One application for such soft implants is for reconstruction or augmentation of the female breast. Other potential applications for implants that would benefit from having a textured surface are also considered to be within the scope of the invention.

Figure 1A:
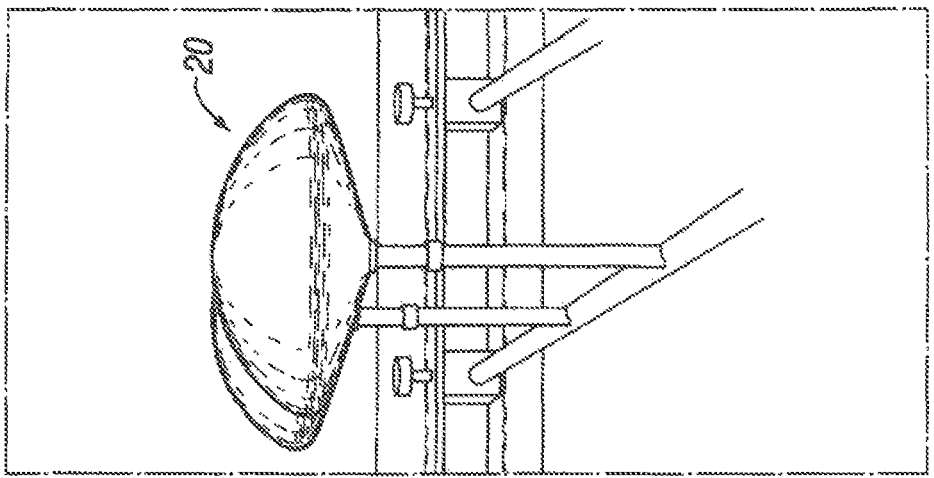
FIGS. 1A-1C illustrates one process for forming flexible implant shells for implantable prostheses and tissue expanders.
Figure 1B:
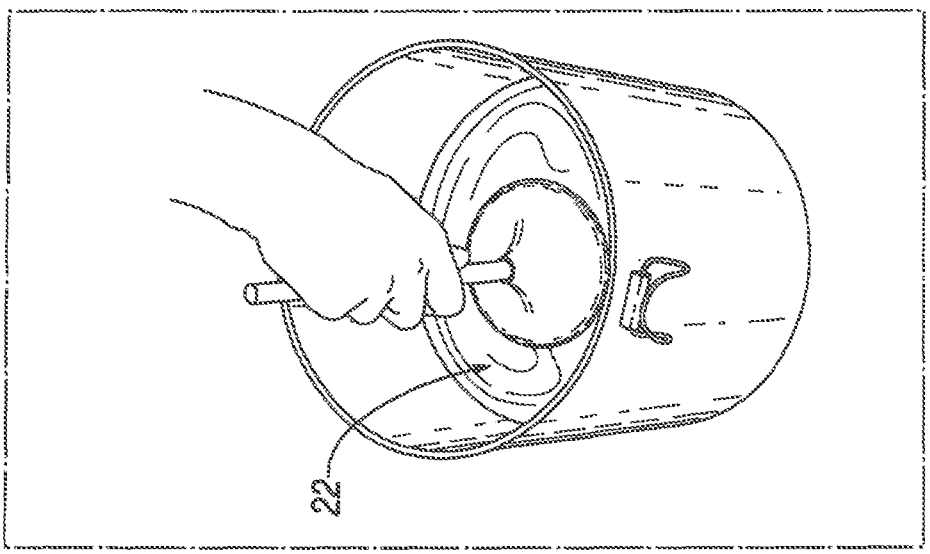
Figure 1C:
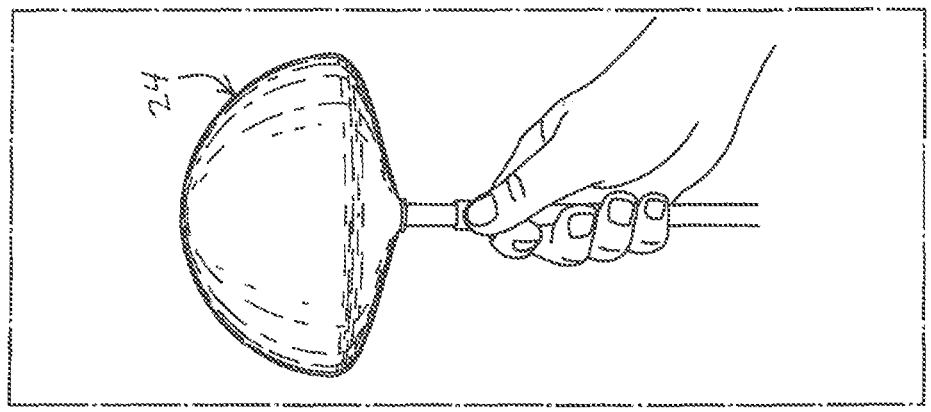

FIGS. 1A-1C illustrates one conventional process for forming flexible implant shells, useful as components of the present invention, for implantable prostheses and tissue expanders. The process typically includes dipping a suitably shaped, e.g. breast implant-shaped, mandrel 20 into a liquid elastomer, e.g. a silicone elastomer dispersion 22. This method may make up some of the preliminary steps in accordance certain embodiments of the invention.

The elastomer dispersion may comprise a silicone elastomer and a solvent. The silicone elastomer may be any suitable biocompatible silicone elastomer, for example, polydimethylsiloxane, polydiphenyl-siloxane or some combination of these two elastomers. Typical solvents include xylene or trichloromethane. Different manufacturers vary the type and amount of the ingredients in the dispersion, the viscosity of the dispersion and the solid content of the dispersion. Nonetheless, the present invention is expected to be adaptable to have utility with a wide variety of elastomers.

The mandrel 20 is withdrawn from the dispersion and the excess silicone elastomer dispersion is allowed to drain from the mandrel. After the excess dispersion has drained from the mandrel, at least a portion of the solvent is allowed to volatilize or evaporate. This may be accomplished by flowing air over the silicone-coated mandrel at a controlled temperature and humidity. Different manufacturers use various quantities, velocities or directions of air flow and set the temperature and humidity of the air at different values. However, the desired result, driving off the solvent, remains the same.

The dip and volatilize procedure may be repeated (e.g., repeating of the steps shown in FIGS. 1B and 1C) a number of times so that a number of layers of silicone are built up on the mandrel to reach a desired shell thickness. A layered structure can be made by sequentially dipping the mandrel in different silicone dispersions. Alternatively, the steps may be repeated in a single dispersion so that a finished breast implant shell 24, for example, prior to the texturing, filling and finishing steps, is a single homogenous material or layer. That is, the dipping process may be done in multiple stages or steps, each step adding more material, yet the shell exhibits no distinct layers and the entire shell wall is homogenous or uniform in composition.

Once the elastomer shell has been stabilized, by allowing volatilization, any loose fibers or particles may be removed from of the exterior of the shell, for example, with an anti-static air gun.

At this point, a tack coat layer is sometimes applied to the shell in order to prepare it for a texturing process. The tack coat layer may be sprayed on, or may be applied by dipping the flexible shell on the mandrel into a tack coat material, for example, silicone elastomer dispersion. The shell is immersed into the elastomer dispersion and the mandrel/shell is mounted on a rack for stabilization. The time required for stabilization typically varies between about 5 and about 20 minutes. The tack coat layer may be made using the same material employed in the base layers.

In some prior art processes for texturing implants, after the tack coat layer has been applied, solid salt particles are applied to the tack coat. The solid salt particles are applied by sprinkling particles on the tack coat, or immersing the tack coated shell/mandrel into a fluidized salt particle bath. In this prior art process, the silicone dispersion with salt particles embedded therein, is allowed to stabilize or cure. The salt particles are then removed by placing the shell in a water bath and rubbing the particles out of the silicone shell, thereby resulting in a textured implant shell, which can be filled with silicone gel or saline, and with some further finalizing steps, is packaged for use as a breast implant.

In accordance with one aspect of the present invention, rather than an application of salt particles to the tack coat as generally described herein above, some embodiments of the present invention provides methods of texturing comprising applying a sacrificial material to a tack coat layer by sequential layering of a material to create a desired form or pattern.

In one embodiment, this is accomplished using a computer to create the desired form or pattern from the sacrificial material. The desired form or pattern may be created with computer-aided design technology and/or by using a 3D scanning technology to replicate a desired pattern or form.

Processes in accordance with the invention utilize computer aided manufacturing technology, commonly referred to as solid freeform fabrication (SFF) or layer manufacturing (LM). A LM process typically begins with the representation of a 3-D object using a computer-aided design (CAD) model or other digital data input. These digital geometry data are then converted into machine control and tool path commands that serve to drive and control a part-building tool (e.g., an extrusion head or inkjet-type print head) that forms the object, layer by layer. LM processes are capable of producing a freeform object directly from a CAD model without part-specific tooling (mold, template, shaping die, etc.) or human intervention.

LM processes were developed primarily for producing models, molds, dies, and prototype parts for industrial applications. In this capacity, LM manufacturing allows for the relatively inexpensive production of one-off parts or prototypes, and for subsequent revisions and iterations free of additional re-tooling costs and attendant time delays. Further, LM processes are capable of fabricating parts with complex geometry and interiority that could not be practically produced by traditional fabrication approaches. This is especially beneficial for the present invention, in which complex geometries, and hence complex resulting textured surfaces, for example, on a micron-sized scale, can be produced with high precision, in a manner not possible with conventional methods of texturing.

Examples of LM techniques include stereo lithography (Sla), selective laser sintering (SLS), laminated object manufacturing (LOM), fused deposition modeling (FDM), laser-assisted welding or cladding, shape deposition modeling (SDM), and 3-D printing (3-DP). The latter category includes extrusion and binder deposition technologies.

In one aspect of the present invention, sacrificial material may be "printed" onto the silicone surface of the shell using 3D printing technology, to form a desired pattern or form, which is then removed from the silicone surface to result in a desired surface texture. In some embodiments, the sacrificial material is applied in a predetermined pattern using a computer-controlled deposit mechanism, the predetermined pattern being a model pattern stored in a CAD format.

The sacrificial material may be any suitable material that can be formed on a substrate (e.g. tacky breast implant shell), into a pattern or form, for example, on a micrometer scale, using additive manufacturing technologies, and subsequently removed from the substrate to leave a negative imprint in the desired pattern or form.

After the sequential layering of the sacrificial material, the sacrificial material may then be removed, leaving an imprint or negative space corresponding thereto, for example, cavities and surfaces corresponding to the 3D pattern or form corresponding to the 3D printed sacrificial material.

For example, to perform a print, a machine reads a design from 3D printable file (STL file) and lays down successive layers of material to build the model from a series of cross sections. These layers, which correspond to the virtual cross sections from the CAD model, are joined or automatically fused to create the final shape. One primary advantage of this technique is its ability to create almost any shape or geometric feature. In the breast implant texturing art, this can be especially useful because intricate, well controlled textures, on a micrometer scale, may be created on implant surfaces, for example, textures which provide, at a cell-sized level, a desired architecture for controlling cell ingrowth, collagen fiber development and the like.

In some embodiments of the invention, the method uses binder deposition printing, for example, binder jetting. Such technology may utilize translating powder and binder solutions. U.S. Pat. No. 5,340,656, issued to Sachs et al. describes such a system, the entire disclosure of this document being incorporated herein by this specific reference. A powder-like material (e.g., powdered ceramic, metal, or plastic) is deposited in sequential layers, each on top of the previous layer. Following the deposition of each layer of powdered material, a liquid binder solution is selectively applied, using an ink-jet printing technique or the like, to appropriate regions of the layer of powdered material in accordance with a sliced CAD model of the three-dimensional part being formed. This binder application fuses the current cross-section of the part to previously bound cross-sections, and subsequent sequential application of powder layers and binder solution complete the formation of the desired part.

For example, in embodiments of the present invention utilizing binder deposition printing technology, the sacrificial material may begin as a powder material which is bonded in layers using a suitable binder. The binder may be, for example, any liquid or solution that can be ejected by ejector parts of a binder deposition printing system, and acts to bind the powder material. Suitable binders may include, but are not limited to, aqueous solutions, alcohol, or other suitable liquids. Using binder deposition technology, the printed, bound material is supported at all times during the build process by submersion in surrounding unbound material, which facilitates the production of intricate and delicate geometries. Furthermore, unbound powder can be easily removed and recycled for further use.

For example, the sacrificial material may comprise a sugar. The powder material may comprise a powdered sugar and the binder may comprise a suitable liquid, for example, a starch-containing water. In one embodiment, the sacrificial material is a sugar that is "printed" onto the shell using technology described, for example, in Hasseln, U.S. Patent Publication No. 2013/0034633, which is incorporated herein in its entirety, by this specific reference.

In some embodiments, a system for creating the texture on an implant shell is provided, the system comprising a computer and a texture forming apparatus. The computer may be a general desktop type computer or the like that is constructed to include a CPU, RAM, and others. The computer and texture forming apparatus are electronically connected to a controller.

The texture forming apparatus is used to create the intricate, patterned or formed sacrificial material on the implant shell, as mentioned elsewhere herein.

For example, a printing stratum is applied to the breast implant shell. The printing stratum may comprise a powdered material, such as a powdered salt, sugar, or other suitable material that can be bound with a suitable binder using deposition printing technology.

The texture forming apparatus includes a 3-D printing apparatus. The printing apparatus may include components for moving a carriage along a Y-direction and along the X-direction in a plane defined by the X-axis and the Y-axis, as dictated by the controller. The carriage contains a binder cartridge containing binder material, and a binder ejector. The binder ejector is connected to the controller. The cartridge part and its associated ejector are components of the carriage, and are freely movable in the XY-plane. Binder solution is ejected from the ejector and adheres to the specified region(s) of the printing stratum.

Once it has been "printed" onto the shell, the 3D texturing material (sacrificial material) is allowed to set, if needed. It may then be removed from the shell to leave a texture in the shell, for example, in the case where the texturing material is applied to a tacky, not fully cured, silicone layer on the shell.

Alternatively, prior to removing the sacrificial material, an elastomeric dispersion can be applied, for example, in a fine layer, to the printed sacrificial material, and allowed to set or cure. Thereafter, the sacrificial material can be removed by rinsing the shell in water or other solution to cause the material to dissolve from between the elastomer shell and upper layer.

Figure 2:
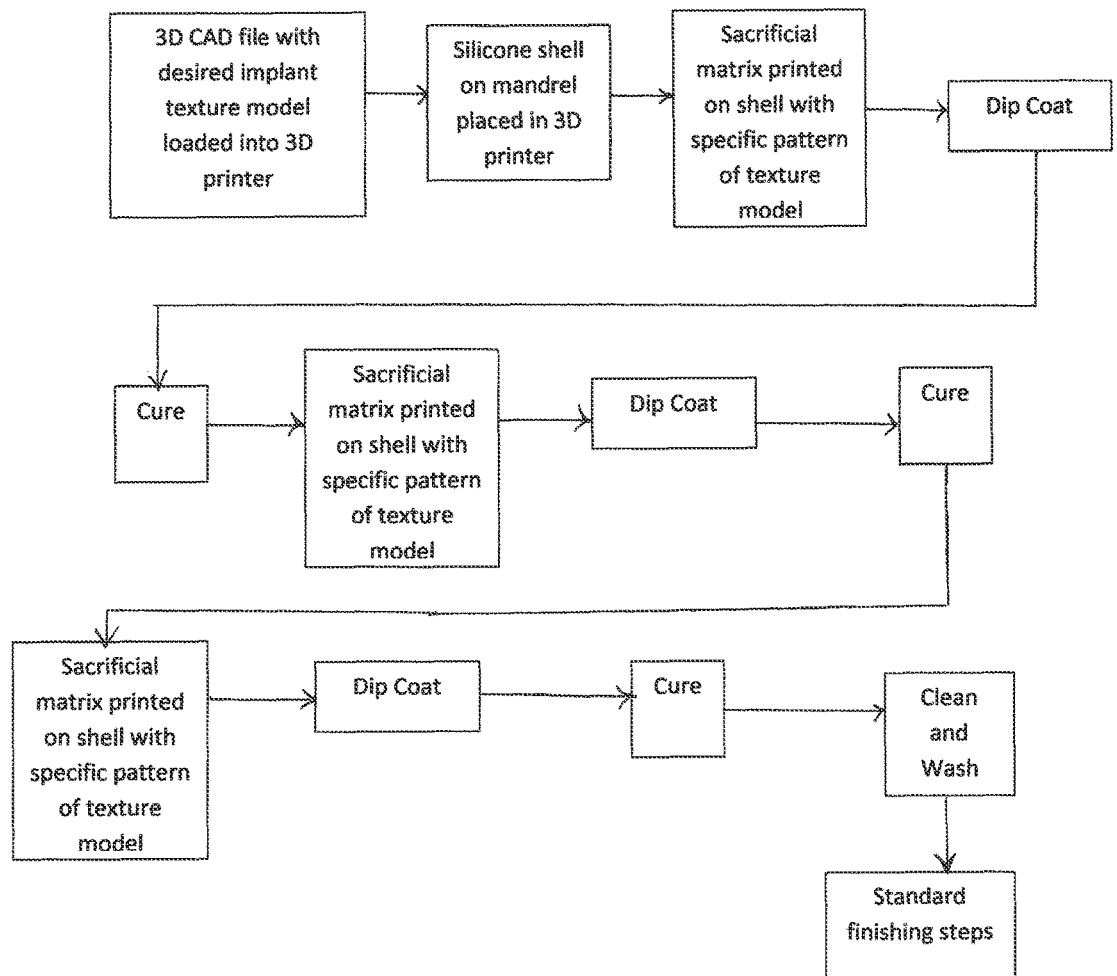
FIG. 2 is a flow chart illustrating a method in accordance with an embodiment of the invention.

Multiple, alternating layers of elastomer and sacrificial material can be applied to a shell to result in texturing having a desired depth or thickness. An example of a method of the invention using alternative layering is illustrated in FIG. 2.

Using the present methods, it becomes possible to vary the texture on the implant in various thicknesses and in various regions of the breast implant shell. For example, there can be areas of the shell having texture, and areas of the shell having essentially no texture, or less texture.

Texture pattern may be varied from "front" to "back" sides of implant. In some embodiments, the texture is provided on the front, or anterior surface, of the implant, and is reduced or even omitted on the back, or posterior surface, of the implant. In this embodiment, breast tissue adherence may be thus enhanced at the front of the implant and may be reduced on the back of the implant where the implant may contact muscle tissue, for example, when the implant is placed subglandularly.

Breast implants may be placed in the breast in one of several different positions, depending on desired outcome, and/or patient and surgeon preference.

In subglandular placement, the breast implant is placed in a surgically formed pocket directly between the glandular breast tissue and the pectoralis major muscle. This placement most approximates the plane of normal breast tissue. In addition, this placement may offer shorter surgery, less pain and discomfort and perhaps a faster recovery. On the downside, subglandular placement may result in a more palpable implant, a higher chance of visible rippling or folding of the implant, and higher risk of capsular contracture.

In submuscular placement, the breast implant is placed beneath the pectoralis major muscle. Thus, the implant is further away from the skin surface and may be less visible or less palpable. This placement may appear more "natural" because the implant is further away from the skin. It may require a longer surgery and recovery period, but is believed to results in a reduced chance for capsular contracture. In breast reconstruction patients where natural breast tissue may be substantially or entirely absent, this placement approach effects maximal coverage of the implant.

Dual plane breast implant placement is a combination approach in which the implant is placed beneath the pectoralis major muscle, after the surgeon releases the inferior muscular attachments. As a result, the upper portion of the implant is partially beneath the pectoralis major muscle, while the lower portion of the implant is positioned in the subglandular plane. This implantation technique may achieve improved coverage of the upper portion of the implant and allow filling of minor laxity of the lower breast.

Accordingly, in some embodiments, the breast implants in accordance with embodiments of the invention, include distinct regions of texturing, some regions including surfaces more conducive to tissue ingrowth, and some regions including surfaces less conducive to tissue ingrowth.

For example, in some embodiments, an anterior surface of the breast implant shell, that is, the surface facing the front of the patient's body, can have a texture made with the presently described methods, and the posterior side of the implant shell, that is, the surface facing the back of the patient's body, can have less texture or no texture. This embodiment may be most beneficial for subglandular placement of the implant.

Figure 3:
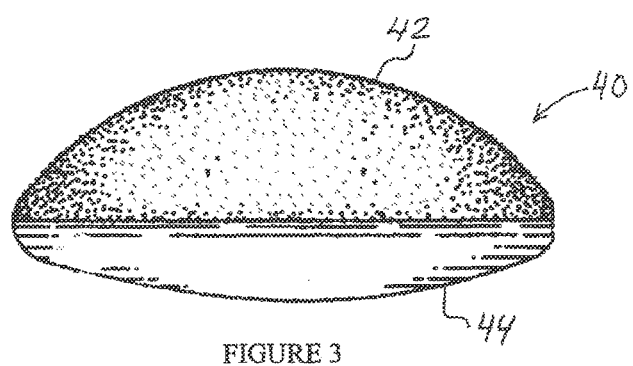
FIG. 3 is a breast implant made using a method in accordance with an embodiment of the invention.

Implant 40, shown in FIG. 3, is an example of an embodiment of the invention. The implant 40 is made using methods described herein. As shown, anterior surface 42 of the implant 40 is textured, for example, using 3D printing techniques. Posterior surface 44 of implant 40 has a reduced texture (relative to the anterior surface), or no texture, or a matte texture.

Alternative embodiments, (not shown) include the reverse, for example, in that the anterior surface has no texture, reduced texture or matte texture, and the posterior surface has enhanced texture. Many other variations of texturing distinct patterns or portions of the implant are contemplated and the invention is not limited to the specific ones described herein. For example, Van Epps, U.S. Patent Publication No. 2013/0261745, describes a dual plane implant with an advantageous surface pattern especially useful for the dual plane breast implant placement surgical technique briefly described above. This patent publication is incorporated herein in its entirety by this specific reference.

The present invention allows for creation of a distinct and precise texture pattern (such as a close packed hexagonal pattern) which is not available using conventional breast implant texturing processes. These and other carefully, precisely designed, specific, repeatable texture patterns may be implemented by the use of 3D CAD files—such as, for example, closed hexagonals, nested/tangent circles, rectangles. Furthermore, each implant size and geometry can be tailored to fit with the use of a 3D texturing model both round and ergonomic shaped implants.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method for creating a textured breast implant, the method comprising:
    dipping a mandrel into a liquid elastomer to form a breast implant shell around the mandrel;
    depositing, via a three-dimensional printing process, a texturing material onto the breast implant shell to form a first micrometer-scale pattern for creating an imprint on the breast implant shell;
    curing the breast implant shell to form a first cured, imprinted layer;
    removing the texturing material from the first cured, imprinted layer to form a textured surface;
    applying a tacky layer onto the textured surface;
    depositing, via three-dimensional printing, additional texturing material onto the tacky layer to form a second micrometer-scale pattern for creating a second imprint on the tacky layer;
    curing the tacky layer to form a second cured, imprinted layer; and
    removing the additional texturing material from the second cured, imprinted layer to obtain a second textured surface, the first and second cured, imprinted layers being configured to permit ingrowth of cells into the breast implant.

2. The method of claim 1, wherein the step of depositing, via a three-dimensional printing process, the texturing material onto the breast implant shell comprises:
    depositing a predetermined number of successive layers of the texturing material; and
    applying to one or more predetermined regions of each successive layer of texturing material a binder that will cause the texturing material to become bonded at said one or more predetermined regions.

3. The method of claim 1, wherein the texturing material comprises a sugar.

4. The method of claim 1, wherein the texturing material comprises a sugar and a binder in an aqueous solution or alcohol.

5. The method of claim 1, further comprising obtaining a predetermined thickness of cured, imprinted layers by applying additional alternating layers of a tacky layer and texturing material.

6. The method of claim 5, wherein the predetermined thickness varies in various regions on the textured surface.

7. The method of claim 1, wherein the first or second micrometer-scale patterns is one of a closely packed hexagonal pattern, a nested/tangent circle pattern, or a rectangle pattern.

8. The method of claim 1, wherein the three-dimensional printing process utilizes binder deposition printing.

9. The method of claim 1, wherein the removing the texturing material from the first cured, imprinted layer comprises placing the shell in a water bath and rubbing the texturing material from the breast implant shell.

10. The method of claim 1, wherein the removing the additional texturing material from the second cured, imprinted layer comprises placing the shell in a water bath and rubbing the additional texturing material from the tacky layer.

11. A method for creating a textured breast implant having a plurality of textured layers thereon, method comprising repeatedly, for each textured layer, performing the steps of:
    applying a tacky layer onto the implant;
    depositing, via a three-dimensional printing process, a texturing material in a predetermined pattern onto the tacky layer of the implant;
    curing the tacky layer; and
    removing the texturing material from the tacky layer to obtain a textured layer.

12. The method of claim 11, further comprising obtaining a predetermined thickness of the textured layer by applying the tacky layer and the texturing material alternately.

13. The method of claim 12, wherein the predetermined thickness varies in various regions on the textured layer.

14. The method of claim 11, wherein the texturing material comprises a sugar.

15. The method of claim 11, wherein the predetermined pattern comprises a micrometer-scale pattern of a hexagonal pattern, a circle pattern, or a rectangle pattern.

16. A method for creating a textured breast implant, the method comprising:
    dipping a mandrel into a liquid elastomer to form a breast implant shell around the mandrel;
    forming a first micrometer-scale pattern on the breast implant shell using sugar and a solid freeform fabrication (SFF) or layer manufacturing (LM) technique;
    curing the breast implant shell to form a first cured, imprinted surface;
    removing the sugar from the first cured, imprinted surface;
    after removing the sugar from the first cured, imprinted surface, applying a tacky layer onto the first cured, imprinted surface;
    forming a second micrometer-scale pattern on the tacky layer using sugar and a solid freeform fabrication (SFF) or layer manufacturing (LM) technique;
    curing the tacky layer to form a second cured, imprinted surface; and
    removing the sugar from the second cured, imprinted surface to obtain a second textured surface that facilitates cell ingrowth on the implant.

17. The method of claim 16, wherein the sugar is applied in a liquid binder solution comprising an aqueous solution or alcohol.

18. The method of claim 16, wherein the removing the sugar from the first cured, imprinted surface comprises placing the shell in a water bath and rubbing the sugar from the first cured, imprinted surface.

19. The method of claim 16, wherein the removing the sugar from the second cured, imprinted surface comprises placing the shell in a water bath and rubbing the sugar from the second cured, imprinted surface.

20. The method of claim 16, wherein the breast implant shell comprises silicone.

* * * * *